United States Patent [19]
Thorens

[11] Patent Number: 6,074,875
[45] Date of Patent: Jun. 13, 2000

[54] MATERIALS AND METHODS RELATING TO THE REGULATION OF POLYPEPTIDE PRODUCTION IN CELLS

[75] Inventor: Bernard Thorens, Epalinge, Switzerland

[73] Assignees: Ecole Polytechnique Federale de Lausanne; Universite de Lausanne; Centre Hospitalier Universitaire Vaudois, all of Lausanne, Switzerland

[21] Appl. No.: 08/912,946

[22] PCT Filed: Feb. 7, 1996

[86] PCT No.: PCT/GB96/00256

§ 371 Date: Mar. 3, 1998

§ 102(e) Date: Mar. 3, 1998

[87] PCT Pub. No.: WO96/25487

PCT Pub. Date: Aug. 22, 1996

[30] Foreign Application Priority Data

Feb. 14, 1995 [GB] United Kingdom .................. 9502830

[51] Int. Cl.[7] .............................. C12N 5/10; C12N 15/63
[52] U.S. Cl. .......................... 435/455; 435/325; 435/354; 435/358; 435/366
[58] Field of Search ................................... 435/325, 354, 435/358, 366, 455

[56] References Cited

FOREIGN PATENT DOCUMENTS

WO 88/10304  12/1988  WIPO .
WO 90/05745   5/1990  WIPO .
WO 93/19175   9/1993  WIPO .

OTHER PUBLICATIONS

Ko and Takano, 1989, "A Highly Inducible System of Gene Expression by Positive Feedback Production of Glucocorticoid Receptors", DNA 8:127–133.

Waeber et al., 1993, "Neuropeptide Y Expression and Regulation in a Differentiated Rat Insulin–Secreting Cell Line", Endocrinology 133:1061–1067.

Widmann et al., "Signal Transduction by the Cloned Glucagon–like Peptide–1 Receptor: Comparison with Signaling by the Endogenous Receptors of β Cell Lines", Mol. Pharm. 45:1029–1035.

*Primary Examiner*—Robert A. Schwartzman
*Attorney, Agent, or Firm*—Mintz, Levin, Cohn, Ferris, Glovsky & Popeo; Ivor R. Elrifi; John T. Prince

[57] ABSTRACT

This application relates to cell lines transfected with (a) nucleic acid encoding one or more hormone receptors, the receptors being capable of transmitting a signal, and (b) nucleic acid encoding a desired polypeptide, the nucleic acid encoding the polypeptide being under the control of a promoter containing regulatory elements responsive to the signal transmitted by the receptor(s) so that transcription of the nucleic acid encoding the desired polypeptide is modulated by the level of the hormone(s) in the patient. Preferably, the receptors are the GIP or GLP-1 receptors controlling the production of insulin in the cells in response to changes in the metabolic status of a patient. The application also relates to compositions comprising these cells and their use in methods of medical treatment.

7 Claims, 5 Drawing Sheets

BASIS FOR THE METABOLIC REGULATION OF INSULIN SECRETION BY ENGINEERED CELLS.

1- Absorption of glucose-containing meal

2- Upon glucose absorption endocrine cells secrete GIP or GLP-1 into the blood circulation

3- Upon GIP and GLP-1 binding to their receptors, the engineered cells produce cAMP which stimulates insulin gene expression and secretion

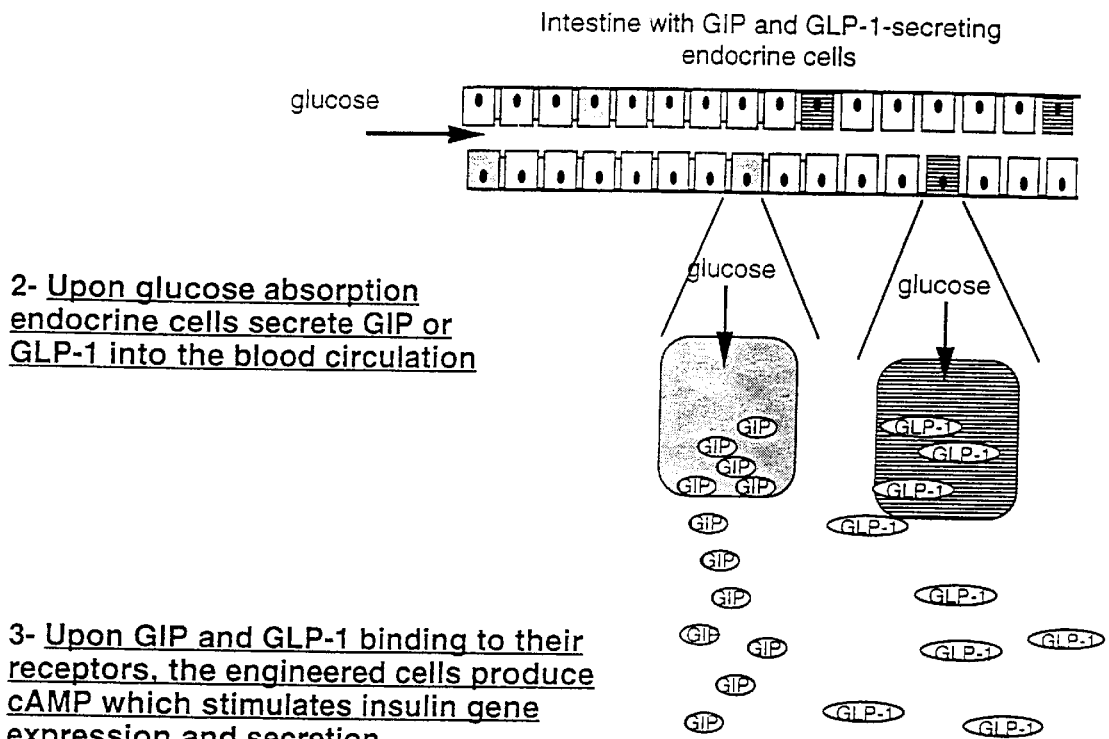

Engineered cells:

 transfected GIP receptor

 transfected GLP-1 receptor

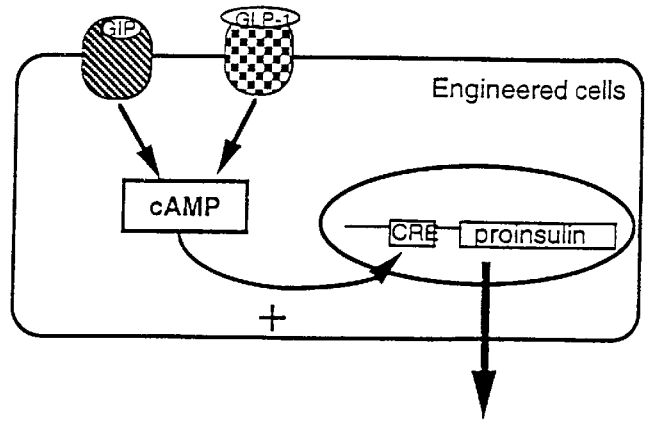

Transfected human insulin gene under the control of a promoter element containing a cyclic AMP responsive element (CRE)

Figure 3

MATERIALS AND METHODS RELATING TO THE REGULATION OF POLYPEPTIDE PRODUCTION IN CELLS

FIELD OF THE INVENTION

The present invention relates to materials and methods relating to the regulation of polypeptide production in cells, and in particular to the expression of polypeptides in cells so that the rate of polypeptide synthesis and secretion from the cells is linked to their environment, for example the metabolic status of the host into which they are transplanted. The present invention also relates to the use of these cells in the preparation of medicaments for the treatment of conditions that respond to the polypeptides.

BACKGROUND TO THE INVENTION

Type I or insulin-dependent diabetes mellitus is the result of the destruction of the patients' insulin secreting cells, the β cells of the pancreatic islets or islets of Langerhans. This destruction is mediated by an immunological process. Current treatment of type I diabetes consists in multiple daily injections of insulin to correct hyperglycemic episodes. This treatment however does not allows a sufficiently tight regulation of blood glucose levels and this lack of moment to moment control of glycemia leads over time to complications such as kidney failure, neuropathy, cardiac diseases and blindness.

Attempts to better control blood glucose could be achieved by transplantation of insulin secreting β cells. Treatment of type I diabetic patients by transplantation of human pancreatic islets has been shown to be possible. However, treatment of a large number of diabetic patients with human islets is impractical due to the limited availability of pancreas from cadaver donors. Pig islets have been proposed as an alternative source for transplantation, but there is currently no way of reliably preparing sufficient pig islets to treat the millions of diabetic patients.

It has been proposed to use insulin secreting cell lines to overcome these problems. Indeed, the availability of insulin secreting cell lines with a proper control of insulin secretion would appear to present a number of advantages, namely the easy expansion of a cell stock and the precise control of the cells quality. Further, in theory, such cell lines could be generated from previously non insulin-secreting cell lines by genetic engineering. However, so far, the cell lines obtained by this approach secrete insulin constitutively or in a manner inappropriately controlled by variations in glucose concentrations (1).

SUMMARY OF THE INVENTION

Broadly, in a first aspect, the present invention provides cell lines transfected with (a) nucleic acid encoding one or more hormone receptors, the receptors being capable of transmitting a signal, and (b) nucleic acid encoding a desired polypeptide, the nucleic acid encoding the desired polypeptide being under the control of a promoter containing regulatory elements responsive to a signal transmitted by the receptor(s) so that transcription of the nucleic acid encoding the desired polypeptide is modulated by the level of the hormone(s). Thus, these cell lines can then be transplanted into patients so that the production of the polypeptide is controlled by hormone(s) produced by the host, thus linking the production of the polypeptide to the need of the host.

In a further aspect, the present invention includes the compositions comprising these cell lines and their use in the preparation of medicaments for the treatment of conditions that respond to these polypeptides, for example by transplanting the cells into a patient. Examples of conditions that can be treated using this approach include diabetes and obesity. In the former case the desired polypeptide is insulin, and in the latter case, the nucleic acid encodes the ob protein or leptin, or encodes glucogen-like peptide I.

The present invention is based on the realisation that for the treatment of diabetes, a key requirement is that the rate of insulin secretion is regulated according to a patient's metabolic status. Accordingly, in one aspect, the invention provides an approach using genetic engineering to link the rate of insulin synthesis and secretion to the metabolic status of the host, based on engineering insulin secreting cell lines with specific plasma membrane receptors. These receptors bind hormones called gluco-incretins, which are released into the blood from intestinal endocrine cells following nutrient absorption. The binding of these hormones to their cognate receptor on engineered cells stimulates insulin gene transcription and secretion by activation of the cAMP second messenger system. However, while the invention is exemplified by an insulin producing cell line, this approach is of general applicability, and can be used in other situations in which precise regulation of the production and/or secretion of the desired polypeptide is needed.

Thus, in one preferred aspect, the present invention provides a cell line transfected with nucleic acid expressing GIP and/or GLP-1 receptors and nucleic acid encoding a desired polypeptide, the latter nucleic acid being under the control of a promoter containing regulatory elements responsive to an intracellular signal transmitted by the receptors so that transcription of that nucleic acid is modulated by the GIP and/or GLP-1. Thus, as GIP and/or GLP-1 are produced in endocrine cells in response to nutrients, this allows the rate of production of the polypeptide, eg insulin, to be linked to the metabolic status of a host of the cells.

The secretion of the polypeptide may also be modulated by GIP and/or GLP-1. Conveniently, the intracellular signal is the production of cAMP, stimulated by GIP or GLP-1 binding to receptors on the cells. In embodiments of the invention using cAMP production as the intracellular signal, conveniently the promoter includes one or more cAMP responsive elements (CREs) that can induce transcription of the nucleic acid encoding the desired polypeptide.

In a further aspect, the present invention provides a cell line transfected with nucleic acid expressing GIP and/or GLP-1 receptor mutants, the mutants capable of producing an intracellular signal different from cAMP on binding GIP and/or GLP-1. Thus, in this aspect, the intracellular signal can stimulate other pathways in the cells, eg to control polypeptide synthesis and secretion by other routes.

In some embodiments, the cells accumulate the polypeptide (eg insulin) as secretory granules, and the intracellular signal is the elevation of intracellular $Ca^{2+}$ levels so that the exocytosis of the secretory granules is stimulated. The cells could also be transfected with nucleic acids encoding GIP and/or GLP-1 receptor mutants which are no longer desensitized. For instance, one possibility is to generate GLP-1 receptor in which the cytoplasmic tail is truncated at position 431 of its amino acid sequence. This mutant receptor is no longer susceptible to homologous and heterologous desensitization and is not internalized following GLP-1 binding (Widmann, C., Dolci, W., and Thorens, B., Mol. Endo. 10: 62–75 (1996)). The use of this mutant receptor will permit a longer lasting production of cAMP following GLP-1 binding and also an increase in the intensity of this signalling response. Similar mutant forms of the GIP receptor can be utilized in combination with the GLP-1 receptor mutants.

In a further aspect, the present invention includes a cell line as defined above for use in methods of medical treatment.

In a further aspect, the present invention provides the use of a cell line as defined above in the preparation of a medicament for the treatment of a condition that responds to the desired polypeptide. Preferably, the hormone receptors are the GIP or GLP-1 receptors so that the production of the polypeptide is linked to GIP or GLP-1 production by the patient. In one embodiment, the polypeptide is insulin and the condition is type I or type II diabetes. In an alternative embodiment, the polypeptide is the ob protein or leptin and the condition is obesity.

Additionally, the present invention provides the use of cell lines as defined above in the preparation of a medicament for the treatment of a condition that responds to the polypeptide contained in secretory granules, wherein the polypeptide is released from the granules by exocytosis stimulated by elevation of the $Ca^{2+}$ level, the elevation being linked to GIP or GLP-1 production by the patient. Preferably, the condition is type I or type II diabetes.

In a further aspect, the present invention provides methods of medical treatment comprising transplanting the cell lines as described above into patients. In the case of cell lines expressing the ob gene, the method of treatment may be a method of cosmetic treatment, eg for reducing body weight.

Typically, in the above aspects of the invention, the nucleic acid encoding the desired polypeptide will be heterologous to the cell into which it is transfected.

Conveniently, the cells used in the present invention are baby hamster kidney (BHK) cells, Chinese hamster ovary (CHO) cells or the mouse myoblast cell line C2C12.

BRIEF DESCRIPTION OF THE FIGURES

The present invention will now be described by way of example by reference to the accompanying drawings in which:

FIG. 3 shows a schematic representation of the proposed genetic engineering system. The different key steps are indicated. 1) Nutrient absorption, in particular carbohydrates such as glucose induces GIP and GLP-1 secretion into the blood from gut endocrine cells. 2) These hormones are released into the blood and reach the transplanted cells. 3) Upon GIP and/or GLP-1 binding, the second messenger cAMP is produced and stimulates transcription of the engineered gene placed downstream of a CRE;

DETAILED DESCRIPTION

The gluco-incretin system

Figure 1A:
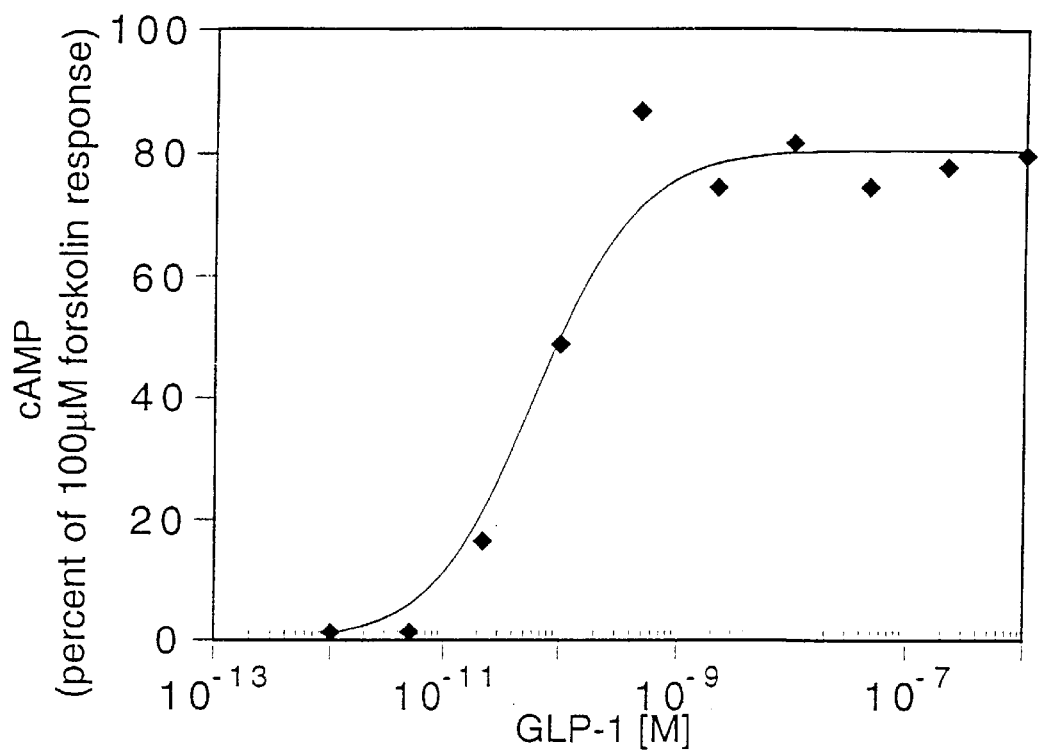
FIGS. 1A–1B show the production of intracellular cyclic AMP by fibroblasts expressing either the human GLP-1 receptor (FIG. 1A) (data from (12)) or two differentially spliced forms of the human GIP receptor (FIG. 1B) (data from (10)) and exposed to different concentrations of their cognate peptides.
Figure 1B:
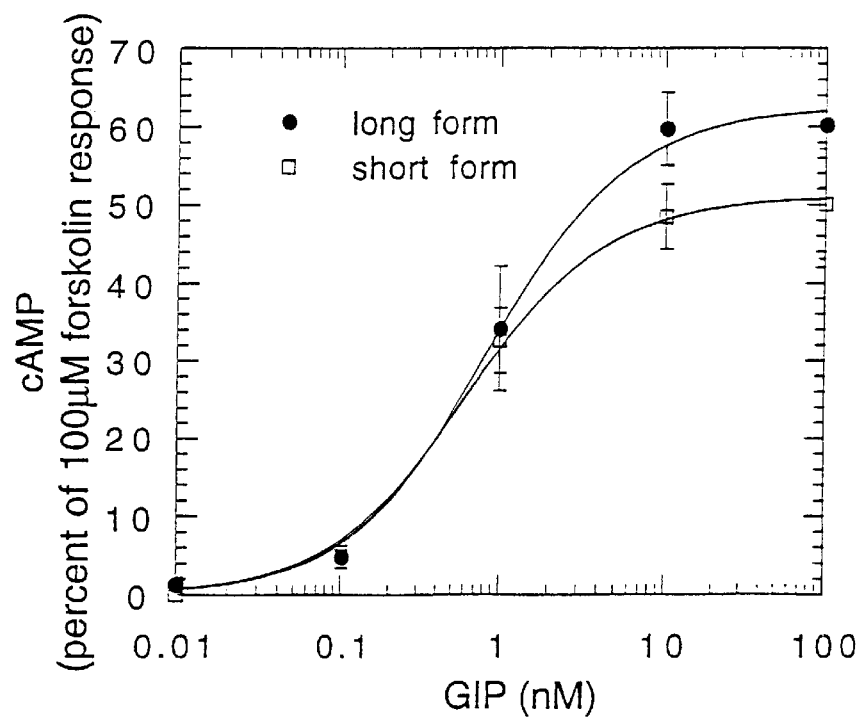

Following nutrient absorption, in particular fat and carbohydrates, endocrine cells present in the intestinal epithelium release in the blood a number of peptidic hormones (2–4). Two of these hormones have a very potent effect on insulin secretion by pancreatic β cells: GIP (gastric inhibitory polypeptide or glucose-dependent insulinotropic polypeptide) (5) and GLP-1 (glucagon-like peptide-1 or insulinotropin) (6,7). These hormones binds to specific receptors on the surface of pancreatic β cells and activate intracellular second messengers. For both the GIP and GLP-1 receptors, the second messenger is 3'-5' cyclic adenosine monophosphate (cAMP). cAMP activates a specific protein kinase, cAMP-dependent protein kinase or protein kinase A. This enzyme phosphorylates a number of key proteins which can then stimulate gene transcription via cAMP response elements present in the promoter region of these genes. This pathway for gene activation by cAMP is present in all cell lines tested. In β cells and other neuroendocrine cells, phosphorylation of some specific proteins of the regulated secretory pathway also stimulates peptide secretion by stimulating the exocytosis of secretory granules (8).

The CDNA clones for both the GIP (9,10) and GLP-1 (11,12) receptor have been recently cloned and functionally characterised. They are membrane proteins with seven transmembrane domains and are coupled to heterotrimeric G-proteins which link activation of the receptor by ligand binding to stimulation of cAMP production.

GIP and GLP-1 secretion is induced by nutrient absorption, in particular fat and carbohydrates for GIP and mostly carbohydrates for GLP-1. The secretion of these peptide in the blood peaks about 30' after nutrient ingestion (2,13). The postprandial secretion of these peptides is unaltered in diabetic patients (4,13).

Experiments and Results

Use of the gluco-incretin system to control insulin synthesis and secretion by genetically engineered cells We investigated the possibility of using isolated GIP and GLP-1 receptor cDNA clones to modify cells previously engineered to express the human preproinsulin (or other hormones) gene under the control of a promoter containing, among other regulatory elements, cAMP responsive elements (CREs). These CREs can be present in single or multiple copies. Expression of the gluco-incretin receptors by these cells will link an increase in extracellular gluco-incretin concentrations to elevations in intracellular cAMP levels and consequently an increase in the transcriptional activity of the gene containing CREs in their promoter regions.

cAMP responsive elements (CREs) have been described in the promoter of a number of genes such as the insulin gene (Philippe, J. and Misottem, M. (1990) J. Biol. Chem 265: 1465–1469) or the corticotropin-releasing hormone gene (Spengler, D., Rupprecht, R., Van, P. P. and Holsboer, F. (1992) Mol. Endo. 6: 1931–1941). These elements consist of a palindromic sequence: TGACGTCA. Production of an oligomer of CREs can be achieved using pairs of complementary synthetic oligonucleotides containing this sequence plus sites compatible with a selected restriction site (XhoI, BamHI or any others). After phosphorylation with T4 polynucleotide kinase and annealing of the complementary oligonucleotides, these are oligomerised by ligation with T4 DNA ligase. The oligomerised structure can then be subcloned by ligation in the chosen position of the expression vector open with the suitable restriction enzyme.

Figure 2A:
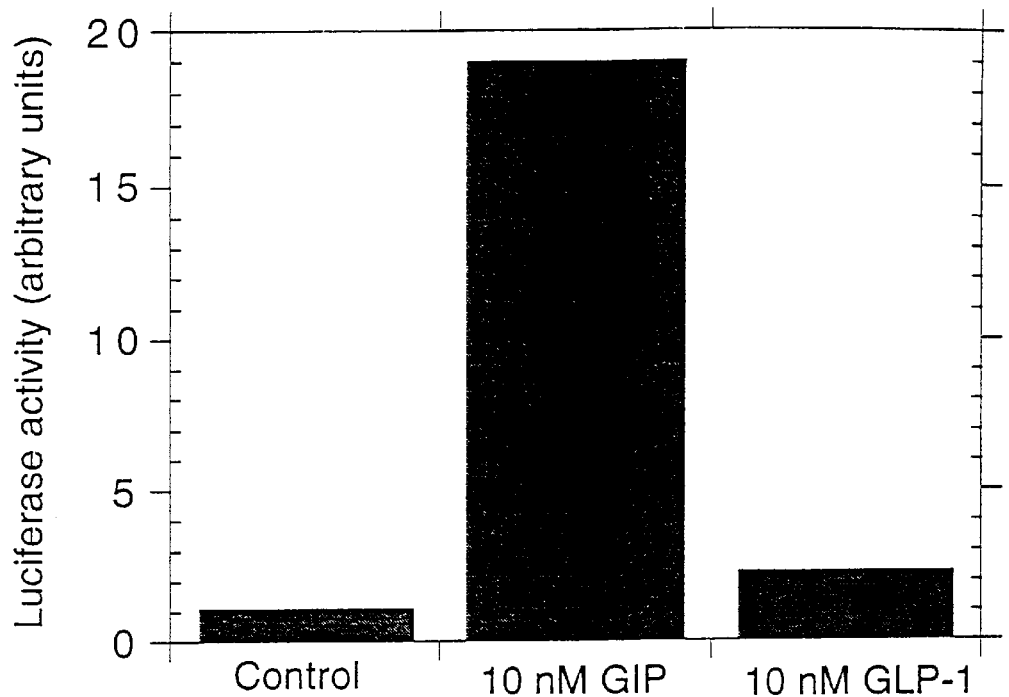
FIGS. 2A–2B show the increase in luciferase activity in fibroblasts expressing the GIP receptor (FIG. 1A) or the GLP-1 receptor (FIG. 1B) and transiently transfected with a reporter gene containing the firefly luciferase gene placed downstream of a promoter containing multiple CREs. Transfection was by electroporation. Assays for luciferase activity was performed 24 hours (FIG. 1A) and 48 hours (FIG. 1B) post transfection. The peptides at the indicated concentrations were present for 4 hours before cell lysis.
Figure 2B:
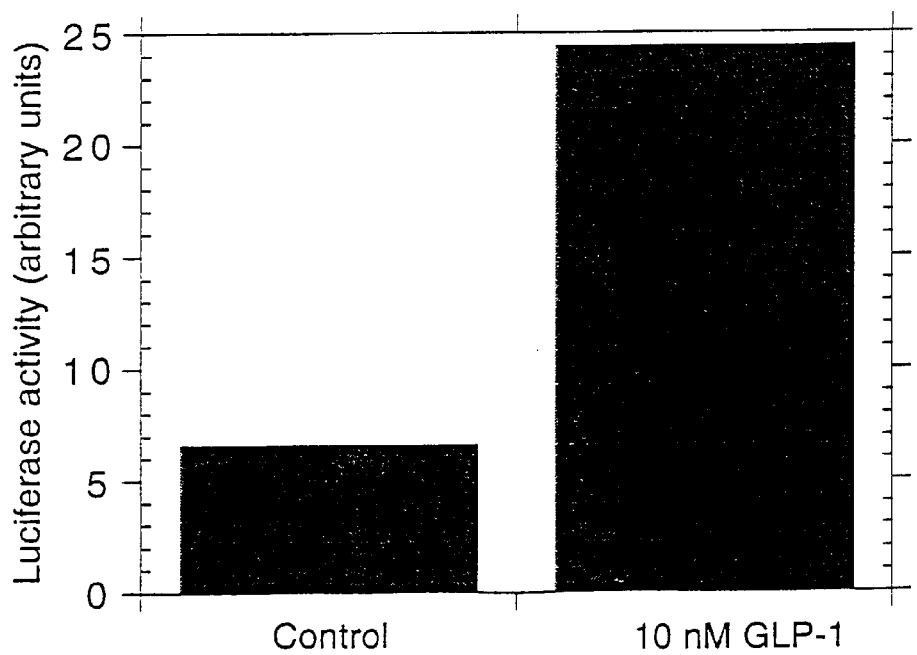

To demonstrate the feasibility of this approach, fibroblast cell lines were stably transfected with the human GIP or GLP-1 receptor. These receptors specifically bind their cognate ligand and, in the presence of increasing concentrations of ligands, there is a sigmoidal dose-dependent accumulation of cAMP as demonstrated in FIG. 1A,B. That the accumulation of cAMP can lead to transcriptional activation of genes containing CRE in their promoter is demonstrated in FIG. 2. In this experiments, fibroblasts cell lines expressing either the GIP or GLP-1 receptor were transiently transfected by electroporation with a DNA construct containing the luciferase reporter gene driven by a promoter containing oligomerized CREs. 24 and 48 hours post transfection, the cells were exposed to GIP or GLP-1 for 4 hours and the luciferase activity measured. Fibroblasts expressing the GIP receptor (FIG. 2A) had increased luciferase activity after exposure to GIP as compared to cells not exposed to the peptide or to cells exposed to GLP-1. This therefore indicates the efficient and specific coupling of GIP binding to its receptor to the transcriptional activation of a CRE containing gene. In FIG. 2B the same experiment was performed 48 hours after electroporation of GLP-1 receptor-expressing cells. Again, a specific increase in luciferase activity was detected after GLP-1 addition.

Figure 4:
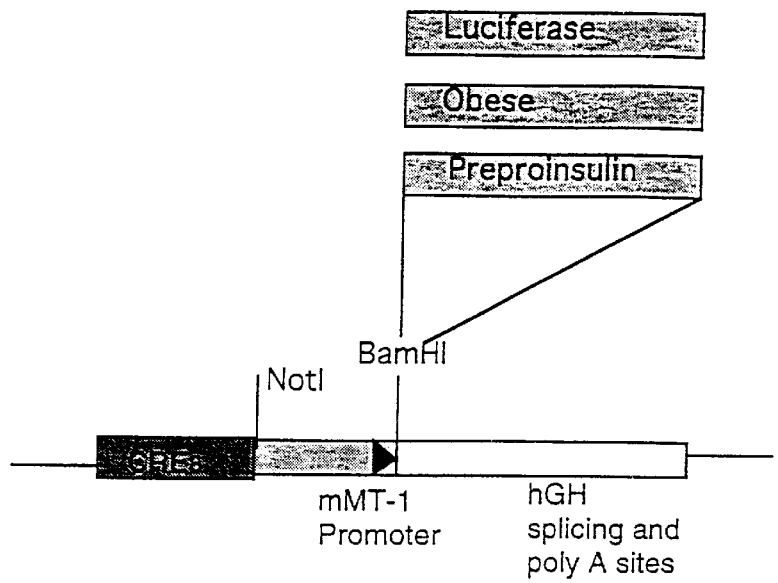
FIG. 4 shows a schematic representation of the nucleic acid vectors used to regulate the expression of different genes.

FIG. 4 shows schematically a vector for transfecting cell lines with nucleic acid encoding a desired polypeptide whose transcription and expression is controlled by multiple CREs. The vector shown contains the mouse metallothionein promoter placed upstream of the cDNA for different genes (firefly luciferase reporter gene, obese (or leptin) gene, preproinsulin gene, or any other gene). The cDNA is followed by human growth hormone gene splicing and polyadenylation signals. Several cAMP-responsive elements (CREs) have been introduced in front of the metallothionein gene. Any other promoter or splicing and polyadenylation signal could be used. This construct is in a plasmid containing a drug-resistance gene (DHFR), neomycin resistance gene, or any other drug resistance gene). The construct can also be co-transfected with another plasmid containing any drug-resistance genes.

Figure 5:
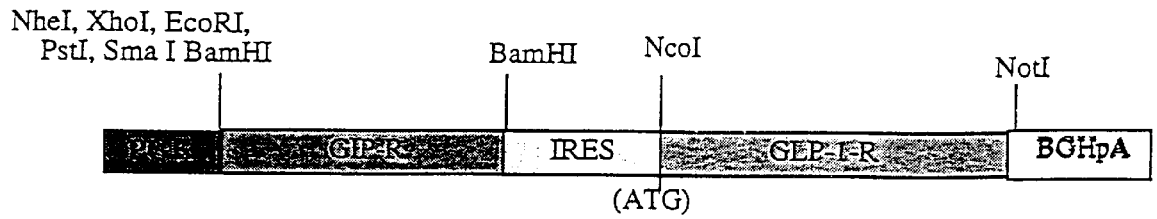
FIG. 5 shows a schematic representation of a nucleic acid vector for the expression of the GIP and GLP-1 receptors.

FIG. 5 shows a vector for the expression of the GIP and GLP-1 receptors. This vector contains the GIP receptor coding sequence (Gremlich et al, Diabetes, 44: 1202–1208, 1995), followed by the internal ribosome entry site (IRES) of the encephalomyocarditis virus (EMCV) which was engineered so that the NcoI site of the virus translation initiation codon (ATG) can be ligated to the translation initiation site of the GLP-1 receptor (Thorens, Proc. Natl. Acad. Sci. USA, 89: 8641–8645, 1992) and in such a way that upstream viral ATGs are mutated to prevent false translation initiation. The GIP receptor cDNA is preceded by the PGK (phosphoglycerate kinase) promoter and followed by human growth hormone gene splicing and polyadenylation signals. The construct is in a plasmid containing a drug-resistance gene (DHFR, neomycin resistance gene, or any other drug resistance gene). The construct can also be co-transfected with another plasmid containing any drug-resistance genes.

Figure 6:
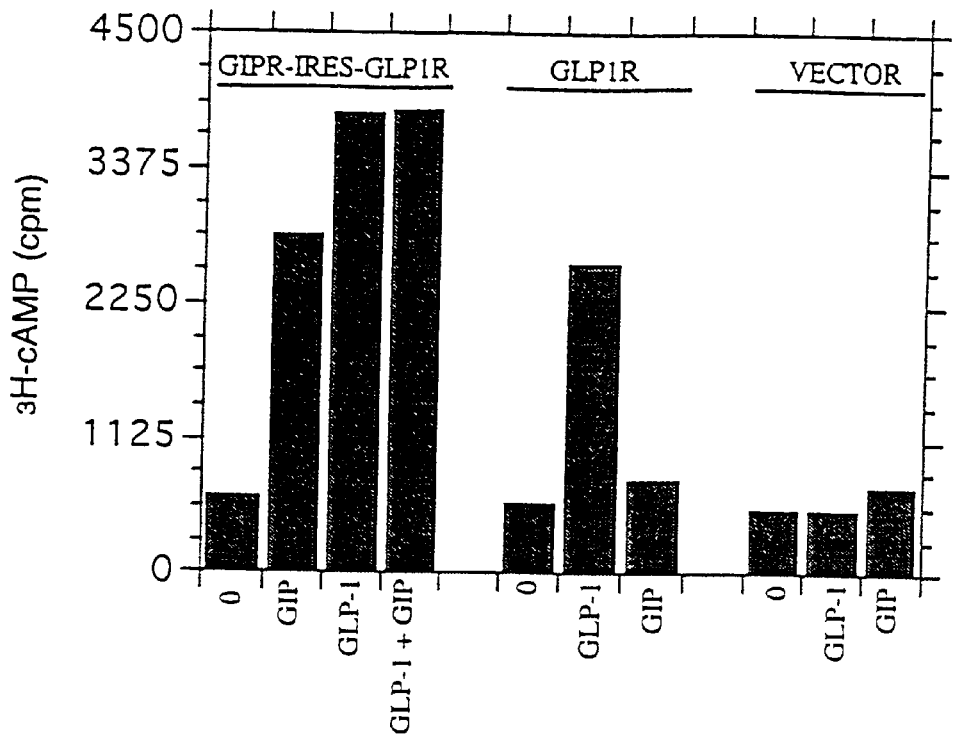
FIG. 6 shows the result of experiments that demonstrate that the GIPR-IRES-GLP1R vector can drive the expression of both receptors at the cell surface in a functional state; and, FIG. 7 shows that myoblast cells stably transfected with the GIPR-IRES-GLP1R construct and the CRE/mMT1/luciferase construct display increased luciferase activity following exposure to GIP.

FIG. 6 shows the results of experiments to demonstrate that when the GIPR-IRES-GLP-1R vector was transfected into cells, it could drive the expression of both receptors on the cell surface in a functional state. In these experiments, Cos cells were transiently transfected with the GIPR-IRES-GLP1R construct described above or with a vector containing only the GLP-1 receptor CDNA (GLP1R) or with an empty vector (vector). Two days later, the cells were incubated in the absence (0) or presence of GIP, GLP-1 or a combination of GIP and GLP-1 all at 10 nM, for a period of 8 minutes and accumulation of cAMP was measured. Cells transfected with GIPR-IRES-GLP1R accumulated cAMP in the presence of GIP or GLP-1 or a combination of both. Cells transfected with the GLP1R construct accumulated cAMP only in the presence of GLP-1, but not GIP. Cells transfected with empty vector did not accumulate cAMP in response to GLP-1 or GIP. These results demonstrate the feasibility of using this system to produce a cAMP intracellular signal that in turn can drive the expression of nucleic acid encoding a desired polypeptide under the control of CREs, such as the vector shown in FIG. 4.

Figure 7:
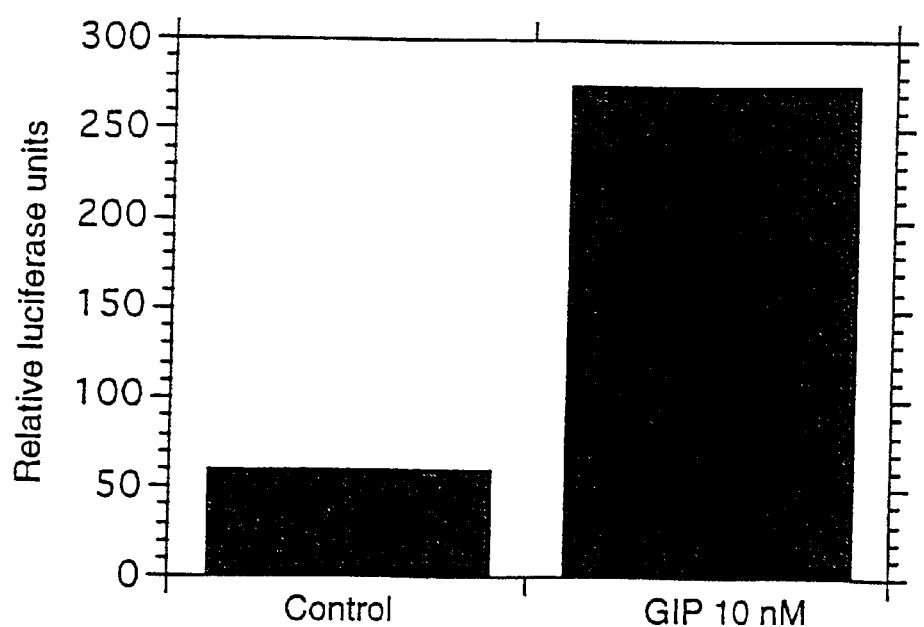

Experiments were then carried out to demonstrate that cells stably transfected with both the GIPR-IRES-GLP-1R and CRE/mMT1/luciferase vectors displayed increased luciferase activity following exposure to GIP. Thus, FIG. 7 shows that exposure of the transfected cells to 10 nM GIP for 4 hours induced 5–6-fold increase in luciferase activity indicating that the genetically engineered cells can display transcriptional regulation of transfected gene expression following exposure to glucoincretin hormones.

Discussion

In these experiments, we have demonstrated that engineering of cell lines to express the receptors for the gluco-incretin hormones GIP and GLP-1 can lead to transcriptional activation of a gene containing CREs in its promoter following exposure of the cells to the specific hormone.

Therefore, engineering cell lines with these receptors could therefore be used to stimulate transcription of any gene provided that its promoter contains CREs. This could be particularly useful in designing peptide- or protein-secreting cell lines for transplantation in human patients and for which the peptide or protein secretion rate should be modulated. In the present example, modulation of gene expression and secretion is modulated by the secretion in the blood of the gluco-incretin hormones. Secretion of these hormones is controlled by nutrient absorption. This system is therefore well suited for the control of insulin secretion by genetically engineered cells since insulin secretion should be stimulated after meal absorption (cf FIG. 3). This system could be extended to the postprandial control of other peptide or protein secretion which could be useful for the management of metabolic disease such as type I or type II diabetes or obesity. In particular, for type II diabetes, the peptidic hormone GLP-1 has been suggested to be a potential new drug for the treatment of postprandial hyperglycemia in place of the currently used sulfonylureas (14–16). The current mode of administration of such peptides is by injection, a method which may offset the potential therapeutic advantages of this peptide. Delivery of the peptide by a transplanted and engineered cell line may therefore be of considerable interest. Our proposed regulated system would provide for a modulated postprandial secretion of GLP-1 from engineered cells which overexpress, for instance, the GIP receptor.

As discussed above, phosphorylation of proteins by cAMP-activated protein kinase may also stimulate secretion of insulin in β cells by a direct effect on exocytosis of insulin-containing (secretory) granules. Engineering of the gluco-incretin receptors in cell lines possessing secretory granules (such as insulinoma, pituitary or other cell lines containing a regulated pathway for peptide or protein secretion) may stimulate secretion via a mechanism distinct from that on gene transcription, ie regulated exocytosis of secretory granules.

Another possible extension of this engineering concept is based on the experimental observation that exocytosis of secretory granules requires elevation in intracellular calcium (17). The gluco-incretin receptors are normally coupled to cAMP. It is known for receptors of the G-coupled receptor family that specific regions of the receptors—usually the third cytoplasmic loop—are involved in coupling to activation of second messengers. Substituting this region of the gluco-incretin receptors for the homologous region of a receptor coupled to elevation in intracellular calcium will change the signalling property of the GIP and GLP-1 receptors. Ligand binding will therefore induce elevations in intracellular calcium instead of cAMP thereby directly stimulating exocytosis of secretory granules.

Obesity is very common in Western societies and often leads to secondary complications such as diabetes or heart diseases. Recently, the gene encoding a satiety factor has been isolated by genetic analysis of the ob/ob obese mouse (18). The product of the ob gene (leptin) is a 167 amino acid polypeptide which has the characteristic of a secreted protein. It is produced by adipocytes and represents a key element in the control of food intake by its action on satiety centres. Earlier physiological studies have indeed shown that the product of the ob gene could cause animals to stop eating and a defect in this gene leads to hyperphagia and obesity.

The use of the ob gene product (leptin) to control appetite and therefore body weight may be of therapeutic use. Due to the relatively large size of the ob polypeptide, a cell therapy approach for delivering the product is certainly attractive. However, for cells transfected with the ob gene to be therapeutically useful, the rate of polypeptide delivery should be controlled so that patients would not stop eating at all. The approach set out above of linking nutrient absorption to increased expression of the transfected gene should therefore be ideal to provide the necessary control of the ob gene production and secretion.

REFERENCES

1. Newgard, C. B. 1994. Cellular engineering and gene therapy strategies for insulin replacement in diabetes. Diabetes 43: 341–350.
2. Ebert, R. and W. Creutzfeld. 1987. Gastrointestinal peptides and insulin secretion. Diab. Met. Rev. 3: 1–16.
3. Unger, R. H. and A. M. Eisentraut. 1969. Enteroinsular axis. Arch. Intern. Med. 123: 261–266.
4. Creutzfeld, W. and M. Nauck. 1992. Gut hormones and diabetes mellitus. Diab. Met. Rev. 8: 149–177.
5. Dupre, J. 1991. Influences of the gut on the endocrine pancreas. An overview of established and potential physiological mechanisms. In The Endocrine Pancreas. E. Samols, editor. Raven Press, Ltd, New York. 253–281.
6. Mojsov, S., G. C. Weir, and J. F. Habener. 1987. Insulinotropin: glucagon-like peptide 1(7–37) co-encoded in the glucagon gene is a potent stimulator of insulin release in the perfused rat pancreas. J. Clin. Invest. 79: 616–619.
7. Hoist, J. J., C. Ørskov, O. Vagn Nielsen, and T. W. Schwartz. 1987. Truncated glucagon-like peptide 1, an insulin-releasing hormone from the distal gut. FEBS 1. 211: 169–174.
8. Thorens, B. and G. Waeber. 1993. Glucagon-like peptide-1 and the control of insulin secretion in the normal state and in NIDDM. Diabetes 42: 1219–1225.
9. Usdin, T. B., E. Mezey, D. C. Button, M. J. Brownstein, and T. I. Bonner. 1993. Gastric inhibitory polypeptide receptor, a member of the secretinvasoactive intestinal peptide receptor family, is widely distributed in peripheral organs and the brain. Endocrinol. 133: 2861–2870.
10. Gremlich, S., A. Porret, H. Hani, D. Cherif, N. Vionnet, P. Froguel, and B. Thorens. 1994. Cloning, functional expression and chromosomal localization of the human pancreatic islet glucose-dependent insulinotropic polypeptide receptor. Diabetes submitted:
11. Thorens, B. 1992. Expression cloning of the pancreatic beta cell receptor for the gluco-incretin hormone glucagon-like peptide I. Proc. Natl. Acad. Sci. USA 89: 8641–8645.
12. Thorens, B., A. Porret, L Buhler, S. -P. Deng, P. Morel, and C. Widmann. 1993. Cloning and functional expression of the human islet GLP-1 receptor. Demonstration that exendin-4 is an agonist and exendin-(9–39) an antagonist of the receptor. Diabetes 42: 1678–1682.
13. Jarousse, C., D. Bataille, and B. Jeanrenaud. 1984. A pure enteroglucagon, oxyntomodulin (glucagon 37), stimulates insulin release in perfused rat pancreas. Endocrinol. 115: 102–105.
14. Nauck, M. A., M. M. Heimasaat, C. Ørskov, J. J. Holst, R. Ebert, and W. Creutzfeld. 1993. Preserved incretin activity of glucagon-like peptide 1 (7–36)amide but not of synthetic human gastric inhibitory polypeptide in patients with type-2 diabetes mellitus. J. Clin. Invest. 91: 301–307.
15. Gutniak, M., C. Ørskov, J. J. Holst, B. Ahren, and S. Efendic. 1992. Antidiabetogenic effect of glucagon-like peptide-1 (7–36)amide in normal subjects and patients with diabetes mellitus. N. Engl. J. Med. 326: 1316–1322.
16. Nathan, D. M., E. Schreiber, H. Fogel, S. Mojsov, and J. F. Habener. 1992. Insulinotropic action of glucagonlike peptide-1-(7–37) in diabetic and nondiabetic subjects. Diabetes Care 15: 270–276.
17. Henquin, J. C., A. Debuyser, G. Drews, and T. D. Plant. 1992. Regulation of K+ permeability and membrane potential in insulin -secreting cells. In Nutrient Regulation of Insulin Secretion. P. R. Flatt, editor. Portland Press, London, Chapel Hill. 173–191.
18. Zhang, Y., Proenca, R., Maffei, M., Barone, M., Leopold, L., Friedmann, J. M., Positional cloning of the mouse obese gene and its human homologue. Nature (1994) 372: 425–432).

What is claimed is:

1. A method of producing a cell line, the cell line expressing a desired polypeptide in response to extracellular gastric inhibitory polypeptide (GIP; glucose-dependent insulinotropic polypeptide) and/or glucagon-like peptide-1 (GLP-1; insulinotropin) hormones; the method comprising the steps of:
   (a) selecting a cell line that does not express the GIP or GLP-1 receptor; and
   (b) transfecting the first cell line of step (a) with nucleic acid encoding GIP and/or GLP-1 receptors, and nucleic acid encoding a desired polypeptide, the nucleic acid encoding the polypeptide being under the control of a promoter containing regulatory elements responsive to a signal transmitted by the receptor(s) caused by binding of GIP or GLP-1 wherein transcription of the nucleic acid encoding the desired polypeptide is modulated by GIP and/or GLP-1 binding to the receptor(s).

2. The method of claim 1 wherein the GIP or GLP-1 receptors produce cAMP in response to GIP or GLP-1 hormone binding to the receptors and the regulatory elements of the promoter are cAMP responsive elements (CREs).

3. The method of claim 1 wherein the desired polypeptide is insulin.

4. The method of claim 1 wherein the desired polypeptide is the ob gene product or leptin.

5. A cell line produced by the method of claim 1.

6. The method of claim 1 or claim 2 where the hormone receptor is a GLP-1 receptor mutant which is truncated at amino acid 431.

7. The cell line of claim 5 the cell line expresses insulin in response to extracellular GIP and/or GLP-1 hormones.

* * * * *